United States Patent
Besson

(10) Patent No.: US 9,835,730 B2
(45) Date of Patent: Dec. 5, 2017

(54) PROJECTION DATA BINNING AND IMAGE GENERATION IN PHOTON COUNTING IMAGING MODALITY

(75) Inventor: Guy M. Besson, Danvers, MA (US)

(73) Assignee: Analogic Corporation, Peabody, MA (US)

( * ) Notice: Subject to any disclaimer, the term of this patent is extended or adjusted under 35 U.S.C. 154(b) by 205 days.

(21) Appl. No.: 14/387,279

(22) PCT Filed: Mar. 30, 2012

(86) PCT No.: PCT/US2012/031436
§ 371 (c)(1),
(2), (4) Date: Sep. 23, 2014

(87) PCT Pub. No.: WO2013/147843
PCT Pub. Date: Oct. 3, 2013

(65) Prior Publication Data
US 2015/0069257 A1    Mar. 12, 2015

(51) Int. Cl.
A61B 6/00 (2006.01)
G03B 42/00 (2006.01)
(Continued)

(52) U.S. Cl.
CPC ............ G01T 1/17 (2013.01); A61B 6/463 (2013.01); A61B 6/465 (2013.01); A61B 6/469 (2013.01);
(Continued)

(58) Field of Classification Search
CPC .................. G01T 1/17; G01T 1/1647
(Continued)

(56) References Cited

U.S. PATENT DOCUMENTS 6,411,670 B1    6/2002  Besson
2006/0284098 A1  12/2006  Vija
2011/0235774 A1*  9/2011  Dolazza ............... A61B 6/502
                                        378/11

FOREIGN PATENT DOCUMENTS

WO    9721113 A2    6/1997
WO    2005091216 A2  9/2005
(Continued)

OTHER PUBLICATIONS

Int. Preliminary Report cited in PCT Application No. PCT/US2012/031436 dated Oct. 1, 2014, 8 pgs.
(Continued)

Primary Examiner — David Porta
Assistant Examiner — Carlyn Igyarto
(74) Attorney, Agent, or Firm — Cooper Legal Group, LLC

(57) ABSTRACT

Among other things, one or more techniques and/or systems are described for presenting images derived from a photon counting imaging modality. Initially, a first image is derived by binning native projection data in a first manner to create first binned data and generating the first image using the first binned data. A region-of-interest within the object may be identified from the first image, and, based upon the identified region-of-interest, the native projection data may be rebinned in a second, different, manner to create second binned data. Because the second manner of binning the native projection data is different than the first manner, an image resulting from the second binned data may be different than the first image. Moreover, a user interface may be provided for assisting a user in selecting a region-of-interest and/or for specifying desired properties of the second image.

16 Claims, 4 Drawing Sheets

(51) Int. Cl.
*G06T 3/40* (2006.01)
*G01T 1/17* (2006.01)
*G01T 1/164* (2006.01)
*A61B 6/03* (2006.01)
*G06T 11/00* (2006.01)

(52) U.S. Cl.
CPC .............. *G01T 1/1647* (2013.01); *G06T 3/40* (2013.01); *A61B 6/03* (2013.01); *A61B 6/032* (2013.01); *A61B 6/037* (2013.01); *G06T 11/003* (2013.01); *G06T 11/005* (2013.01)

(58) Field of Classification Search
USPC .................................................. 250/394, 395
See application file for complete search history.

(56) References Cited

FOREIGN PATENT DOCUMENTS

| | | | |
|---|---|---|---|
| WO | 2008062360 | A2 | 5/2008 |
| WO | 2010062291 | A1 | 6/2010 |

OTHER PUBLICATIONS

Korean Office Action cited in Japanese Application No. 2015-503170 dated Dec. 1, 2015, 2 pgs.
International Search Report cited in related application No. PCT/US2012/031436 dated Dec. 19, 2012, p. 4.

\* cited by examiner

PROJECTION DATA BINNING AND IMAGE GENERATION IN PHOTON COUNTING IMAGING MODALITY

BACKGROUND

The present application relates to the field of radiology imaging. It finds particular application to radiology imaging modalities that can employ photon counting techniques. For example, medical, security, and/or industrial applications may utilize a computed tomography (CT) scanner or a projection radiography imaging modality (e.g., a digital radiography imaging modality) to count a number of X-ray and/or gamma photons that traverse an object under examination and that are detected by a photon counting detector array. Based upon the number of photons detected, one or more images providing a two-dimensional representation, three-dimensional representation, four-dimensional representation (e.g., dynamic three-dimensional representation) and/or five-dimensional representation (e.g., dynamic multi-spectral three-dimensional representation) of an object under examination may be generated therefrom.

Today, CT and other radiology imaging modalities (e.g., single-photon emission computed tomography (SPECT), mammography, projection radiography, etc.) are useful to provide information, or images, of interior aspects of an object under examination. Generally, the object is exposed to radiation comprising photons (e.g., such as X-rays, gamma rays, etc.), and an image(s) is formed based upon the radiation absorbed and/or attenuated by the interior aspects of the object, or rather an amount of photons that is able to pass through the object. Generally, highly dense aspects of the object absorb and/or attenuate more radiation than less dense aspects, and thus an aspect having a higher density, such as a bone or metal, for example, will be apparent when surrounded by less dense aspects, such as muscle or clothing.

Radiology imaging modalities generally comprise, among other things, a detector array comprised of a plurality of detector cells that are respectively configured to convert radiation that has traversed the object into electrical signals that may be processed to produce the image(s). The cells are typically "chargeinteg-rating" and/or "photon counting " type cells (e.g., the imaging modality operates in charge integration mode, photon counting mode, or both).

Photon counting cells are configured to convert energy into electrical signals that are proportional to the energy of a detected photon (e.g., at times referred to as a detection event). Thus, ideally, signals produced by respective cells generally comprise one or more current and/or voltage pulses, for example, respectively associated with a single detection event. A controller may then be used to determine the location and energy of respective detection events, accumulate the detection events occurring during a measurement interval (e.g., an "acquisition view"), digitize the information, and/or process the digital information to form an image, for example. It may be appreciated that there are numerous advantages to photon counting cells over charge integrating cells. For example, the counting of photons is substantially devoid of electronic noise (e.g., apart from the inherent random nature of photon emissions, which may be modeled by a Poisson random variable). Therefore, a lower dose of radiation may be applied to the object under examination. Moreover, photon counting cells generally allow for energy or wavelength discrimination. Therefore, images resulting from radiation emitted at different energy levels may be obtained at the same or substantially the same time, for example.

SUMMARY

Aspects of the present application address the above matters, and others. According to one aspect, a method for use in a photon counting radiology imaging modality is provided. The method comprises binning native projection data yielded from a photon counting detector into a first set of bins to create first binned data and generating a first image of an object using the first binned data. The method also comprises identifying a region-of-interest in the object from the first image and rebinning at least a portion of the native projection data into a second set of bins based upon the region-of-interest to create second binned data. The method further comprises generating a second image of the object using the second binned data, the first image different than the second image.

According to another aspect, a system for use in a photon counting radiology imaging modality is provided. The system comprises a binning component configured to bin native projection data yielded from a photon counting detector array into a first set of bins to create first binned data from which a first image of an object is generated and configured to rebin at least a portion of the native projection data into a second set of bins to create second binned data, from which a second image of the object is generated, based upon an identified region-of-interest in the object as identified from the first image.

According to yet another aspect, a computer readable storage medium comprising computer executable instructions that when executed via a processor perform a method for use in a photon counting radiology imaging modality is provided. The method comprises binning native projection data yielded from a photon counting detector into a first set of bins to create first binned data and generating a first image of an object using the first binned data. The method also comprises identifying a region-of-interest in the object from the first image and rebinning at least a portion of the native projection data into a second set of bins based at least in part upon the region-of-interest to create second binned data. The method further comprises generating a second image of the object using the second binned data, the first image different than the second image.

FIGURES

The application is illustrated by way of example and not limitation in the figures of the accompanying drawings, in which like references indicate similar elements and in which.

DESCRIPTION

Figure 1:
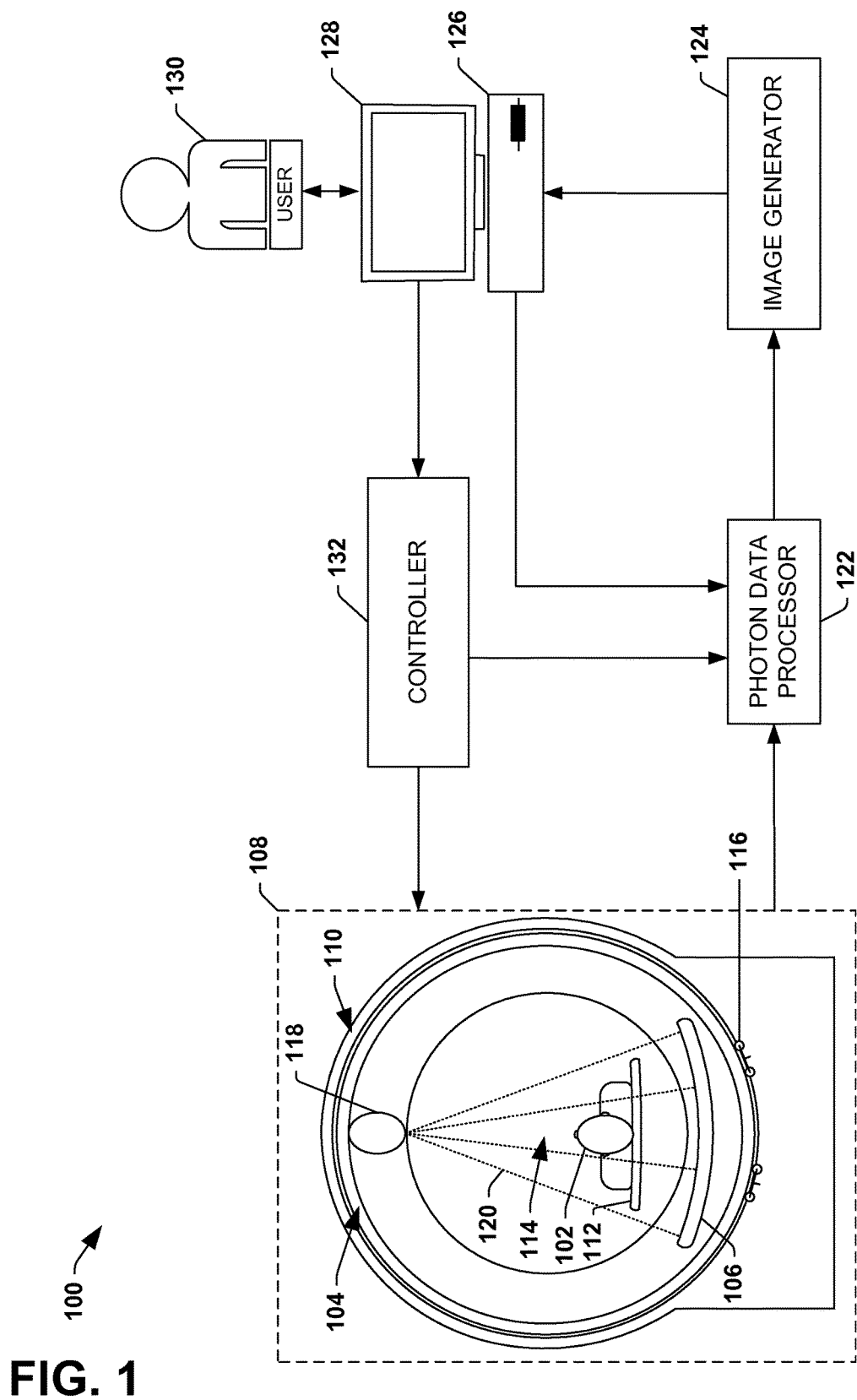
FIG. 1 is a schematic block diagram illustrating an example examination environment for examining an object.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

It may be appreciated that in radiology imaging, photons are emitted by a radiation source in a fundamentally independent manner. That is, the emission of one photon at a given time by a source does not provide information regarding the likelihood of emission of another photon in a subsequent interval of time. Such processes may be modeled by a Poisson random variable. Accordingly, in radiology imaging, the recording of one photon at a particular spatial location and a particular time may not provide imaging information. Thus, in projection imaging, image information may be obtained based upon spatial intensity differences of cells, where the intensity of photons detecting by respective cells are recorded over a given interval of time. In computed tomography, image information may be obtained based upon, for example, a simplified mono-energetic model, where line integrals of attenuation coefficients (μ) are estimated by $$\int_{Path\ L} \mu(l)\,dl = -\ln\left(\frac{I}{I_0}\right).$$

More particularly, with respect to projection imaging, diagnostic information may be conveyed by spatial intensity differences across image pixels, the intensity at respective pixels (indexed by i) being recorded over a given interval of time (Δt). In the absence of noise and gain variations, the intensity at pixel i can be modeled by (for charge-integrating technology) $I_i = \Sigma_j n_j E_j$, where $E_j$ is the energy of incoming photons (or representative energy of a j-th energy bin) and $n_j$ is the number of photons at that energy (or energy bin of average energy $E_j$), for example. Since variations in intensity across a projection image may be meant to carry diagnostic information, variations in detector cell response, such as due to dark current offset and/or gain, incoming radiation flux variations, etc., may be, to the extent possible, subtracted or compensated for. The residual intensity variations being then understood to originate from within the patient or object being imaged, for example. Although not typically specified or clarified, the model typically assumes an under-lying process of binning the data in the spatial dimensions, with a sum (integration) taking place across the spatial detector pixel dimensions Δx, Δy and along the time dimension, typically corresponding to one sample integration time (Δt). Accordingly, a more detailed model for a charge-integrating imaging modality (still leaving out gain variations, incoming flux variations, and dark current, etc.) may be given by $I_i = \int_{\Delta y}\int_{\Delta x}\int_{\Delta t}(\Sigma_j n_j E_j)\,dx\,dy\,dt$. Thus it may be apparent that four binnings typically take place in projection imaging (e.g., which typically occurs in the analog domain). Note that charge-integrating technologies typically bin photons with respect to energy by attributing a weight to respective photons that is proportional to energy. It may be appreciated that the quantity $\Sigma_j n_j E_j$ may be related to an incoming radiation flux, to a radiation spectrum, to a patient or object attenuation along a specific volume defined by the source area and the pixel area, and/or to scattered radiation, for example. Because of a requirement for normalization, the recording of radiation photons on an individual basis (such as in a photon-counting modality) may also require binning, to allow for meaningful interpretation of spatial variations across an image, for example.

More specifically, with respect to computed tomography, and in a single-spectrum application, the line integrals of the attenuation coefficients (μ) are estimated by $$\int_{spectrum} I(E)\exp\left\{-\int_{Path\ L}\mu(l,E)\,dl\right\}dE = -\ln\left(\frac{I}{I_0}\right),$$

where $I_0$ is for example, depending on the modality, either the number of incoming photons for the measurement or the total intensity associated with the incoming photons for the measurement: $I_0 = \int_{spectrum} I(E)\,dE$, with either $I(E)=n(E)$ or $I(E)=n(E)\times E$. The measurement is typically defined by an area of the radiation source, a recording cell area, and a sampling time interval Δt. The area of the radiation source and the recording cell area may together define a volume through which emitted photons travel, for example. Once again, it is to be understood that the detection of a single photon by itself does not typically carry diagnostic information. Therefore, binning, to allow normalization to a reference flux ($I_0$), may be implemented to define an estimate of the line integral along path (L), which in turn may form the basis for CT image reconstruction, for example.

Photon-counting (e.g., sometimes referred to as single photon counting) is a detection technology that ideally counts every radiation photon impinging upon a detector focal plane (e.g., a detection surface of a detector array) and potentially records an estimate of the energy of respective photons at a time of detection/arrival. Because detected photons are respectively labeled with time-of-arrival information (e.g., which may be accurate to within a few hundred nanoseconds), and because the size of respective detector cells may be as small as one-hundred microns squared or smaller, for example, there exists the potential for high temporal and/or spatial resolution images. Moreover, the potential to estimate the energy of respective photons may lead to improved CT numbers (e.g., density value assigned to a voxel in a volumetric image) and/or to improved multi-spectral (e.g., multi-energy, such as dual-energy) imaging modalities.

The potential spatial, temporal, and/or energy resolution benefits of photon-counting also come with an information processing cost. By way of example, a photon-counting detector array of a CT imaging modality with a time resolution of 100 nano-seconds and a number of energy bins (e.g., with cells measuring about 100 microns squared, for example) may produce 200,000 more samples per second than a conventional, charge-integrating detector array of a CT imaging modality (e.g., with cells measuring about 1 millimeter squared, for example). As such, the volume of information acquired from a photon-counting detector array during an examination of an object may be significantly greater than the volume of information acquired from a conventional, charge-integrating detector array. Given the volume of information acquired from a photon-counting detector array, it may be neither practical nor desirable to display all possible information of an image derived therefrom. For example, monitors have a finite number of addressable pixels and the processing time/resources to generate an image using all possible information may be too great to be feasible. As such, the information yielded from cells may be binned along spatial, temporal, and/or energy dimensions and images may be generated using the binned data. Determining how to bin such data and/or what data to bin has been a challenge because different applications may prefer the data to be binned differently. Further, within a given application, different imaging tasks, such as for example, the detection of a lung nodule, or the estimation of a lung nodule volume, may optimally require specifically prescribed data binning modes. Moreover, it may be desirable to change how data is binned according what is identified in an initial image of an object under examination. For example, in a security application, a metal object appearing in an initial image of a suitcase under examination may warrant a closer inspection. Therefore, in may be desirable to change how the data is binned (e.g., without reexamining the object) to provide a more detailed image that focuses on the metal object, for example.

It may be appreciated that binning with regard to charge-integrating imaging modalities is typically performed per device specifications (e.g., such as X-ray source size, detector cell area, and/or sampling time interval(s)). Thus, aside from pre-scanning protocol choices dictating CT helical pitch, rotation time, and/or number of views per rotation, for example, binning of the projection data in charge-integrating imaging modalities typically does not occur as a function of either user input and/or as a function of specifics of the anatomy/object of interest.

Accordingly, among other things, one or more systems and/or techniques are described herein for identifying a region-of-interest in an object under examination from a first image and for rebinning projection data based upon the identified region-of-interest to generate a second image that depicts the region-of-interest differently in a photon counting imaging modality. By way of example, and not limitation, a user-interface may be provided that comprises a region-of-interest (ROI) window. The region-of-interest window may be configured to selectively overlay a portion of the first image and to be maneuvered about the first image to identify/select a region-of-interest (e.g., where the boundaries of the window define outside boundaries of the region-of-interest). When a region-of-interest is identified/selected, a menu may be presented providing options for changing the appearance of the region-of-interest (e.g., from how it appears in the first image). As an example, the menu may provide for reducing artifacts that appear in the region-of-interest, increasing a spatial resolution of the region-of-interest, increasing a contrast resolution of the region-of-interest, and/or displaying the region-of-interest in a multispectral image (e.g., if the first image is merely a density image). Based upon the identified region-of-interest and/or a selection of one or more of the provided options, for example, the projection data may be rebinned in such a manner that it causes a desired change in the appearance of the region-of-interest from the first image to the second image. It may be appreciated that the foregoing features are merely example features intended to describe one embodiment of the systems/techniques described herein. Other features and/or embodiments may be realized in view of the following disclosure.

FIG. 1 is an illustration of an example environment 100 of an example imaging modality that may be configured to generate data (e.g., images) representative of an object 102 (e.g., a patient, luggage, etc.) or an aspect thereof under examination. It may be appreciated that the example configuration is merely intended to be representative of one type of imaging modality (e.g., a third-generation CT scanner) and is described herein merely as an example arrangement of an example imaging modality. That is, the disclosure, including the scope of the claims, is not intended to be limited to a particular type(s) of radiography imaging modality(ies) to the extent practical, but rather the systems and/or techniques described herein may be used in conjunction with a wide variety of radiography imaging modalities, such as, but not limited to, CT, SPECT, mammography, and/or projection radiography, for example. Moreover, the placement of components is merely intended to be provided as an example and may not necessarily detail possible arrangements and/or configurations. For example, in one embodiment, the photon data processor 122 may be mounted on a rotating gantry 104 of the imaging modality.

In the example environment 100, an examination unit 108 of the imaging modality is configured to examine one or more objects 102. The examination unit 108 can comprise a rotating gantry 104 and a (stationary) support structure 110 (e.g., which may encase and/or surround as least a portion of the rotating gantry 104 (e.g., as illustrated with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise one or more radiation sources 118 (e.g., an ionizing X-ray source or other ionizing radiation source) and a photon counting detector array 106, comprised of a plurality of photon counting cells, that is mounted on a substantially diametrically opposite side of the rotating gantry 104 relative to the radiation source(s) 118.

During an examination of the object(s) 102, the radiation source(s) 118 emits fan, cone, wedge, and/or other shaped radiation 120 configurations from a focal spot(s) of the radiation source 118 (e.g., a point or small area/volume within the radiation source(s) 118 from which radiation 120 emanates) into the examination region 114. It may be appreciated that such radiation 120 may be emitted substantially continuously and/or may be emitted intermittently (e.g., a short pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 can comprise a linear or two-dimensional array of photon counting cells disposed as a single row or multiple rows in the shape of a circular, cylindrical, or spherical arc, for example, typically having a center of curvature at the focal spot of the radiation source(s) 118, for example. As the rotating gantry 104 rotates, the detector array 106 is configured to directly convert and/or indirectly convert detected radiation into electrical signals.

The detector array 106 is generally operated in a photon counting mode (e.g., as opposed to a charge integration mode). That is, the cells are of a photon counting type and are configured to convert energy (e.g., in the case of CT scanners, X-ray energy) into electrical signals that may be proportional to the energy of detected photons (e.g., where the detection of respective photons may be referred to as a detection event and/or the like). Thus, signals produced by respective cells generally comprise one or more current and/or voltage pulses, for example, respectively associated with a single detection event. Moreover, because the signals are generally proportional to the energy of detected photons, it may be appreciated that the components analyzing the signals may have the ability to determine/estimate respective energies of detected photons. However, in some embodiments, the respective energies of detected photons may not be determined/estimated.

Signals that are produced by the detector array 106 or rather by photon counting cells comprised within the detector array 106 may be transmitted to a photon data processor 122 that is in operable communication with the detector array 106. The photon data processor 122 (e.g., which may also be referred to as a controller) is configured to receive the signals and generate native projection data indicative of, among other things, a location and detection time for respective photons detected by the detector array. The detection times of respective photons may respectively correlate to a particular known position of the radiation source(s) 118 at those detection times.

It may be appreciated that in some instances (e.g., because of practical limitations of the photon data processor 122 as described above), it may be impractical and/or undesired to present all or substantially all information associated with the native projection data. For example, in some imaging modalities, such as CT, it may be impractical because of the large volume of data that would need to be transferred across a data-link from the rotating side of the gantry 104 to the stationary side of the imaging modality. It may also be impractical because a display (considered in combination with a human observer's visual system) cannot typically convey the depth of information (e.g., grey levels) in one setting and/or does not typically have the appropriate addressable pixel size. Therefore, the photon data processor 122 may bin the native projection data into a first set of bins based upon temporal, spatial, and/or energy information derived from respective detection events to create first binned data. For example, in one embodiment, the photon data processor 122 may initially bin the native projection data by detection time to create a first set of temporal bins. That is, stated differently, the photon data processor 122 may be set to bin the photons that were detected within particular time interval together and determine an approximate position of the radiation source 118 during that interval of time (e.g., which may be referred to as an acquisition view and/or the like). It may be understood that the number of temporal acquisition bins, which respectively correspond to an acquisition view, should be relatively large to reduce tangential blurring (e.g., caused when respective bins represent photons emitted during a larger span along the trajectory or movement of the radiation source(s) 118).

It may be appreciated that "binning" and/or the like is used herein in a broad sense to imply processing of data. For example, in a simile form, binning may comprise summing and/or averaging the data. However, the binning should also be understood to comprise more general processing, such as linear and non-linear processing. For example, generalized linear processing may comprise weighting and adding, matrix processing, and/or convolving. Non-linear processing in one simple form, may include clipping and thresholding, and binary decisions, for example. More generally, various forms of non-linear processing are of interest in radiology imaging, including sorting, non-linear functions and combinations such as when considering an exponential model, for example.

It may be appreciated that the projection data may be indicative of other characteristics of the detected photons besides detection time and/or location. For example, the projection data may include information related to an energy of detected photons and/or a trajectory/angle of respective photons from the radiation source(s) 118 to the detector array 106 (e.g., which may be derived by the photon data processor 122 based upon the location of a detected photon, the time it was detected, and a position of the radiation source(s) 118 when the photon was detected).

Further, as will be described in more detail below, the photon data processor 122 may be configured to receive information (e.g., feedback) that causes the native projection data to be rebinned to create second binned data (e.g., in real-time as a user is viewing an image generated from the first binned data). By way of example, in one embodiment, using an image generated from the first binned data, a region-of-interest may be identified in an object under examination. Based upon the identified region-of-interest, the photon data processor 122 may rebin at least a portion of the native projection data, to provide for presenting the region-of-interest differently (e.g., in a second image). For example, using the second binned data, an image may be generated with a better a spatial and/or contrast resolution of the region-of-interest (e.g., relative to an image generated from the first binned data), for example. It will be appreciated that although the photon data processor 122 is illustrated as being on the stationary portion of the imaging modality, in some embodiments, it may be located within and/or attached to the rotating gantry 104. As such, the transfer of the native projection data to the stationary side of the imaging modality may not be necessary to create the second binned data (e.g., and/or a second image) as a function of the identified region-of-interest.

It should also be noted that the features described herein with respect to the photon data processor 122 may not be necessary/utilized in charge-integrating imaging modalities. That is, binning of the native projection data is not necessary to generate images, nor is it typically done except per pre-imaging protocol choices as described above (e.g., because, as described above, in charge-integrating modalities the native data is already the result of binning or integration processes (typically perform in the analog domain)). This is in contrast to the photon-counting imaging modalities, where (while respective detection events are labeled with spatial and temporal information) little to no diagnostic information can be ascribed to such detection events until binning of the data has been specified due to the fundamentally statistical nature of radiation photon emissions and detection as described above. Thus, in photon-counting imaging modalities, image processing and display and/or image reconstruction, may not take place until the data has been binned, such as in a desired manner, for example, and preferably as a function of the object data itself, as determined either from projection data characteristics, from image data, and/or from a combination of image data and projection data.

The example environment 100 also illustrates an image generator 124 that is operably coupled to the photon data processor 122 and is configured to generate one or more images representative of the object 102 under examination using suitable analytical, iterative, and/or other image generation techniques (e.g., tomosynthesis reconstruction, filtered-back-projection, iterative reconstruction, image processing, etc.) based upon the binned data. That is, the image generator 124 generates an image of (e.g., representing) an object under examination as a function of the binned data. Thus, an image created from the first binned data may have a different appearance than an image created from the second binned data (e.g., even if the same native projection data is included in both the first and second binned data but sorted differently).

The example environment 100 also includes a terminal 126, or workstation (e.g., a computer), configured to receive image(s) from the image generator 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input (e.g., such as imaging protocols, user preferences, protocol-dependent user preferences, etc.) which can direct operations of the object examination apparatus 108 (e.g., a speed of gantry rotation, an energy level of the radiation, etc.) and/or can receive user input regarding the selection of a region-of-interest, for example, from an image displayed on the monitor 128, for example.

In the example environment 100, a controller 132 is operably coupled to the terminal 126. In one example, the controller 132 is configured to receive user input from the terminal 126 and generate instructions for the examination unit 108 indicative of operations to be performed. For example, the controller 132 may be utilized to instruct the examination unit 108 when to begin and/or end an examination and/or to direct movement of a support article 112 (e.g., such as a conveyor belt), for example. Moreover, the controller 132 may receive a selection of a region-of-interest from the terminal 126 and may convey such information to the photon data processor 122 (e.g., or the terminal 126 may be in direct communication with the photon data processor 122), for example.

It may be appreciated that the example component diagram is merely intended to illustrate one embodiment of one type of imaging modality and is not intended to be interpreted in a limiting manner. For example, the functions of one or more components described herein may be separated into a plurality of components and/or the functions of two or more components described herein may be combined into merely a single component. Moreover, the imaging modality may comprise additional components to perform additional features, functions, etc.

Further, it will be appreciated that while the binning is described with respect to CT imaging, it may apply to other imaging performed via radiation, including, for example, X-ray projection imaging, such as digital mammography, fluoroscopy, and the like. That is, a similar data binning may (must) take place, as the image information is carried through image intensity modulations that should correspond to anatomical/density variations. Stated differently, as previously described, little to no diagnostic meaning may be ascribed to the detection of a single photon via photon-counting. Instead, photons may be binned at least temporally and/or energy-wise to enable meaningful interpretation of the spatial variations across the image. For example, in one embodiment, binning may comprise image and data processing to decrease the data dynamic range and to effectively increase the image contrast, for example, thus allowing presentation and visual perception of more information content in a display with limited gray level dynamic range, for example.

Figure 2:
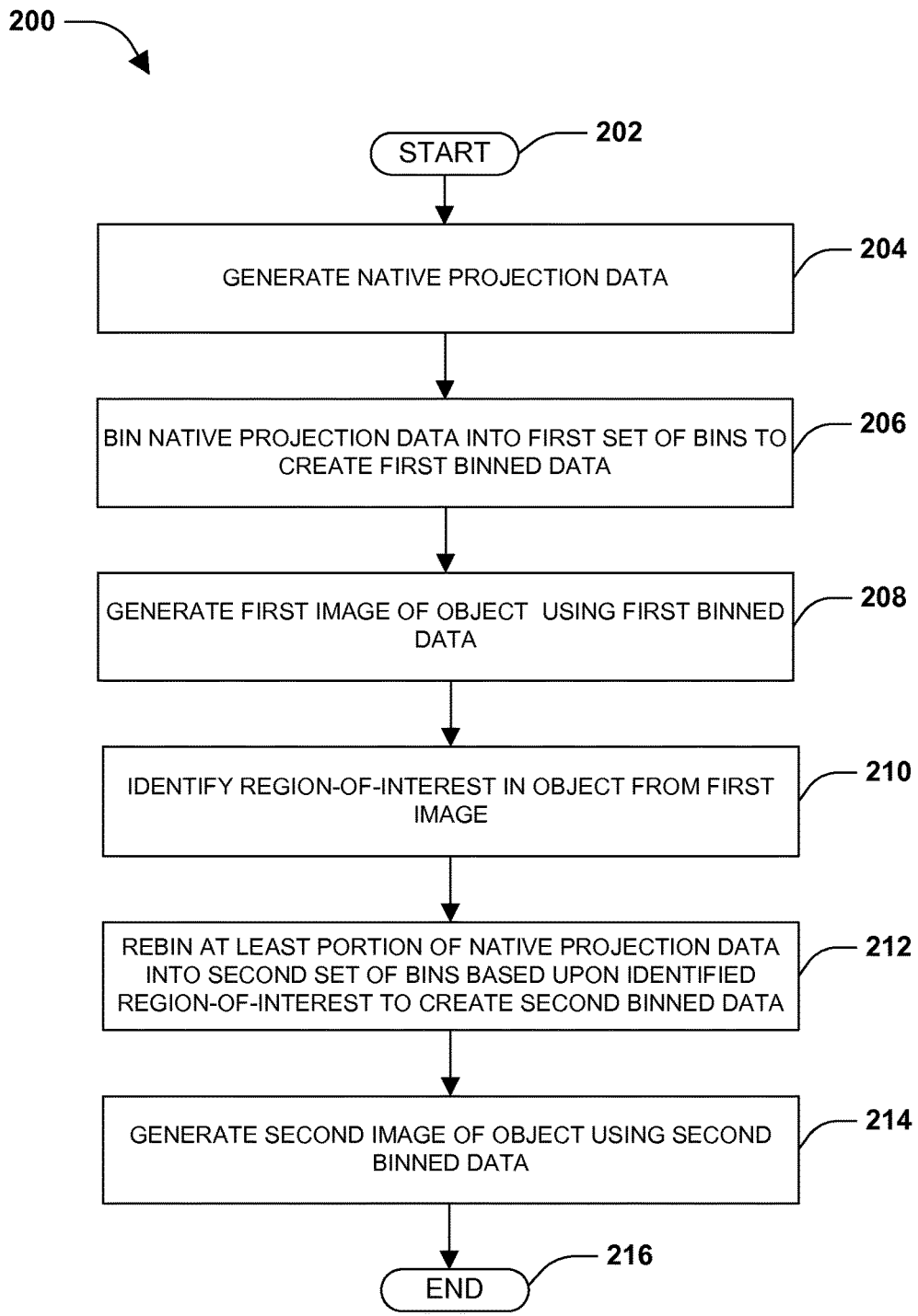
FIG. 2 is a flow diagram illustrating an example method for use in a photon counting radiology imaging modality.

FIG. 2 illustrates a flow diagram of an example method 200 for use in a photon counting radiology imaging modality to generate a second image of an object based upon a region-of-interest identified from a first image of the object. By way of example, using such a method 200, medical personnel may identify a potentially malignant tumor in a patient and may focus on a region of the patient comprising the potential tumor, as represented in a first image, to generate a higher resolution image of the region comprising the potential tumor (e.g., without having to re-irradiate the patient). It may be appreciated that, as will be described in more detail below, such a technique may do more than merely enlarge a region-of-interest (e.g., where interpolation is performed on the first image to generate an enlarged image (e.g. which maintains a same resolution as the first image)). For example, the grouping/binning of native projection data and/or the selection of native projection data to be utilized to generate the second image may be varied relative what is used to generate the first image (e.g., which does not occur in a typical enlargement). That is, image processing/generation becomes interactive, essentially real-time per inputs obtained via image review.

The example method 200 begins at 202, and native projection data is generated at 204. By way of example and not limitation, native projection data may be generated from the conversion of electrical signals produced by photon counting cells of a photon counting detector array. That is, stated differently, during the examination of an object, radiation, such as X-ray radiation and/or gamma radiation, may be emitted from a radiation source towards the object under examination. Radiation that traverses the object may be detected by the detector array, or more particularly by photon counting cells of the detector array. Such cells may be configured to directly convert and/or indirectly convert the detected radiation into electrical signals, which may be processed via an analog-to-digital converter to produce native projection data. Such projection data may be indicative of, among other things, spatial, temporal, and/or energy aspects of the detected radiation. That is, the projection data for respective detection events (e.g., a record of each photon detected) may be indicative of which cell(s) detected the photon, a time when the photon was detected, and/or an approximate energy of the detected photon.

It may be appreciated that the phrase "native projection data" is used broadly herein to refer to projection data that is generated from the detection of photons. Such native projection data may be acquired directly from the conversion of electrical signals to digital data and/or may be acquired post one or more processing acts. For example, in one embodiment, storage constraints may require that the raw digital data be filtered and/or otherwise manipulated before it can be stored and/or further transmitted to components of the imaging modality. Such filtered/manipulated data may also be referred to herein as native projection data (e.g., and typically is the result of filtering/manipulation that occurs prior to the data being binned such that native projection data is what is utilized during a binning process). Therefore, as used herein, the phrase "native projection data" is intended to refer to the raw data, the filtered/manipulated data, and/or both.

Further, it may be appreciated that while reference is made to generating an image of an object under examination, it may be appreciated that the examination may or may not occur concurrently with the binning, generating, and/or presentation of an image representing the object. For example, the native projection data may be stored in a storage device (e.g., hard drive) for several weeks (e.g., or longer) before it is binned and/or generated to create an image. As such, when the raw projection data cannot be stored due to hardware/software limitations of the storage device, for example, the raw projection data may be filtered/manipulated for storage on the storage device as native projection data. Although, again, for purposes herein, it is immaterial whether native projection data refers to the raw data or the filtered/manipulated data. Similarly, where raw projection data can be stored, such raw data can be stored for any amount of time before being used as native projection data, which can likewise be stored for any amount of time before being used to generate, reconstruct, etc. a first image and/or a second image as provided herein (e.g., any amount of time can exist between creation of the first image and the second image).

At 206 in the example method 200, the native projection data is binned into a first set of bins to create first binned data. For example, as previously described, it may be undesirable, impractical, and/or meaningless to present all available information derived from the native projection data in a single image due to, among other things, pixel limitations of a monitor presenting the image and/or processing capabilities. Thus, the data may be binned to reduce computation requirements during image generation, for example, and/or to present an image that appears similar to images a user is presently familiar with viewing. By way of example, and not limitation, users of charge integrating type CT imaging modalities may be familiar with viewing an image that correlates to detector cells that measure approximately 1 millimeter squared. However, respective cells of a photon counting detector array may have a much smaller detection surface (e.g., measuring 100 microns squared). As such, at 206, the native projection data acquired during a measurement interval may be binned such that respective bins represent a 1 millimeter square area of the detection surface. That is, stated differently, at 206, data yielded from a first plurality of adjacent detector cells, representing a 1 millimeter square of the detection surface, during a measurement interval may be grouped together (e.g., to form a bin of data). Similarly, data yielded from a second plurality of adjacent detector cells, representing another 1 millimeter square of the detection surface, during the measurement interval may be grouped together (e.g., to form a second bin of data). In this way, respective sets of binned data comprise data yielded from one or more cells, for example. Similarly, in conventional CT imaging, photon data is binned temporally in projections or views acquired over a fraction of a millisecond, typically in the range of 1 to 0.1 milliseconds such that data produced along the detector arc corresponds to the same time interval. Thus, the native projection data may be temporally binned to form views that correlate to conventional charge-integrating imaging modalities, for example.

It may be appreciated that native projection data may be binned according to any number of properties. By way of example and not limitation, native projection data may be binned into a first set of bins to create first binned data based upon, among other things, temporal, spatial, and/or energy properties of photons represented by the data. Moreover, a combination of properties may be utilized to determine how to bin the native projection data. As an example, in the foregoing example, the projection data is binned as a function of temporal and spatial properties (e.g., but not energy properties). In another embodiment, the native projection data may be binned according to energy properties, for example, such that, when generated, the image may be multi-energy (e.g., creating a z-effective image). In such an embodiment, use of merely one energy bin could then provide data similar to that provided by charge-integrating modalities.

At 208 in the example method 200, a first image of the object is generated using the first binned data. That is, one or more image generation techniques (e.g., back-projection, iterative reconstruction, tomosynthesis reconstruction, image processing, etc.) are utilized to generate an image as a function of the first binned data. It may be appreciated that properties/characteristics of the first image may depend upon, among other things, how the native projection data is binned. For example, an image derived from bins respectively representative of a 1 millimeter squared area of the detector array may have a lower spatial resolution than an image derived from bins representative of a 0.5 millimeter squared area of the detector array.

It may be appreciated that the first image generated at 208 may be a two-dimensional, three-dimensional, four-dimensional, and/or five-dimensional representation of the object depending upon, among other things, an imaging modality that examined the object. For example, where the detector array and/or radiation source are fixed relative to the object during the examination, the projection data acquired may provide for generating/reconstructing merely a two-dimensional image of the object. Conversely, where the detector array and/or radiation source are rotated relative to the object (or where the object is rotated relative to the source/detector; or more generally, when some kind of relative motion takes place between the radiation source, the object to be imaged, and the detector array), volumetric projection data may be acquired and may provide for generating/reconstructing a two-, three-, four- or five-dimensional image/representation of the object. It may be appreciated that the fourth dimension may refer to a time dimension, such that a four-dimensional image is a three-dimensional, dynamic representation, for example. Further, the fifth dimension may refer to an energy dimension, such as when a dynamic, time-dependent four-dimensional data set is provided at respective selected energies and/or energy ranges, for example.

At 210 in the example method 200, a region-of-interest is identified in an object from the first image. More specifically, the first image is reviewed or scanned to identify a region-of-interest in the object as represented in the first image. The region-of-interest may comprise a portion of the object represented in the first image and/or may comprise substantially the entire object represented in the first image (e.g., the ROI may comprise the entirety of the first image or a portion thereof). Such a review/scan may occur manually (e.g., by a user) and/or automatically (e.g., via computer-implemented software). By way of example, in one embodiment, a monitor may display the first image and the user may maneuver a region-of-interest window over the first image to select a region of the object that is of particular interest to the user. In another embodiment, the first image may be reviewed and/or scanned by a computer program, for example, to identify a region-of-interest (e.g., to identify a representation of a desired aspect of the object). As another example, in the context of a security application where baggage is examined, a threat detection system may analyze the first image to identify a possible threat item (e.g., such as based upon a shape of the item, a density of the item, a chemical composition of the item, etc.). If a possible threat item is identified in the first image, a region comprising the possible threat item may be labeled/identified as a region-of-interest (e.g., and further imaging may be performed as described herein). Similarly, in the context of a medical application, a detection system may analyze a first image to identify potential tumors and/or to identify particular aspects of a patient (e.g., a particular muscle or organ). If an object of interest (e.g., a tumor, particular organ, etc.) is identified, a region comprising the object of interest may be labeled/identified as a region-of-interest. In this way, a portion of an image representing a region-of-interest (e.g., and underlying native projection data represented by the portion of the image) may be identified to narrow the scope of focus (e.g., to focus the computations performed to merely a portion of the data that is of particular interest), for example.

At 212 in the example method 200, at least a portion of the native projection data is rebinned into a second set of bins based upon the identified region-of-interest to create second binned data. That is, the native projection data and/or a portion thereof is reorganized to cause a different image (representative of at least the region-of-interest) to be produced. By way of example, the native projection data may be rebinned to cause respective bins of the second set to represent merely a 0.5 mm squared area of the detection surface (e.g., as opposed to a 1 mm squared area of the detection surface as represented in the first set of bins at 206).

It may be appreciated that in one embodiment, less than all of the native projection data may be rebinned to create the second binned data. By way of example, in one embodiment, native projection data that is not representative of the region-of-interest may be excluded from being rebinned at 212 because the projection data is related to a portion of the object that is not of interest (e.g., such that merely native projection data corresponding to the region-of-interest is rebinned). In this way, the amount of data that is utilized for image generation may be reduced (e.g., reducing the computational cost of image generation) while improving one or more aspects of an image (e.g., such as spatial and/or contrast resolution) (e.g., which typically increase computational cost). Although, in another embodiment, all or substantially all of the native projection data may be rebinned into the second set of bins, with the native projection data merely being organized in a different manner than it was organized during the binning at 206.

Alternatively, in another embodiment, native projection data that is not representative of the region-of-interest may be utilized in the image generation leading to a second image at the level of binning provided for to obtain the first image, while projection data that is directly representative of the region-of-interest may be rebinned in a specific, different way as compared to the binning that led to the first image; the binned data sets together contributing to the second image. Moreover, image generation of a region-of-interest may involve projection data that are not directly representative of the region-of-interest (e.g., such as in filtered-backprojection reconstruction, for example). Further, it may be necessary/beneficial to combine the data outside the region-of-interest projection at a third level of binning, that is, at a level of binning different from that used to provide the first image and different from that used for a second image within the direct region-of-interest projection.

Further, the manner in which that native projection data is rebinned to create the second binned data may be a function of a desired change in how the region-of-interest is represented in images. By way of example and not limitation, it may be desired that a second image, resulting from the rebinned projection data, depict the region-of-interest in a higher spatial and/or contrast resolution, depict fewer artifacts in the region-of-interest, alter the representation from a multi-spectral representation (e.g., a z-effective image) to a single-spectral representation (e.g., a density image), and/or alter the representation from a single-spectral representation to a multi-spectral representation. Thus, in one embodiment, at least a portion of the native projection data may be rebinned based upon a region-of-interest and desired properties of a second image representing the region-of-interest, for example.

Desired properties of a second image representing the region-of-interest (e.g., relative to properties of the first image) may be determined based upon user input and/or may be determined automatically via computer-implemented software as a function of the features of the region-of-interest as represented in the first image. By way of example, in one embodiment, a menu displaying menu options (e.g., as further illustrated in FIG. 4) for altering an appearance of the region-of-interest, as represented in the first image, may be presented (e.g., such as upon identification of the region-of-interest) and an indication of a selection from the menu options may be received. In such an embodiment, the received indication may be utilized to determine desired properties of the second image, for example.

In another embodiment, the desired properties of the second image may be determined automatically via computer-implemented software. By way of example, upon the identification of a region-of-interest, the region-of-interest, as represented in the first image, may be analyzed to identify features of the region-of-interest. For example, the first image may be analyzed to identify artifacts and/or to identify particular aspects of the object represented in the region-of-interest. Based upon the identified features, it may be automatically determined how to rebin the native projection data at 212 to create the second binned data. By way of example, with respect to a medical application, an analysis of a region-of-interest may reveal that the region-of-interest comprises bone and soft tissue. Given such information regarding the contents of the region-of-interest, it may be automatically determined that a higher contrast image of the region-of-interest (e.g., relative to the first image) may be desirable. Therefore, the native projection data may be rebinned at 212 to cause a second image (generated from the second binned data) to be generated representing the region-of-interest with a higher contrast ratio (e.g., so that bone and soft tissue may be more easily distinguishable from one another). In this example, binning may be performed along the energy dimension to provide for improved differentiation between soft tissues and bone, for example. It is noted that automatic analysis is not limited to automated detection of threat or disease conditions, but may determine optimal or improved parameters for dynamic, interactive, real-time image processing or generating as it relates to and is determined from the region-of-interest as determined from the first image and/or subsequently produced images. In one embodiment, this automatic data analysis may, in turn, be dependent upon user choices and preferences communicated to the automatic processor either before or (dynamically) upon review of an image comprising the region-of-interest.

At 214 in the example method 200, a second image of the object is generated using the second binned data. That is, a second image is produced using analytic, iterative, and/or other image generation techniques. As further described above, given that the second image is generated using the second binned data, as opposed to the first binned data, the second image may be different than the first image. Thus, by manipulating how the underlying native projection data is organized, an image(s) generated therefrom may also be varied. In this way, the second image may represent the region-of-interest with fewer artifacts, may represent the region-of-interest in a different (e.g., higher) spatial resolution, and/or may represent the region-of-interest in a different (e.g., higher) contrast resolution (relative to the first image), for example. Moreover, the second image may provide a multi-spectral representation of the region-of-interest whereas the first image may provide a single-spectral representation of the region-of-interest and/or vice-versa. As another example, and as determined in part from the identified region-of-interest, the native data may be rebinned differently along the spatial, temporal, and energy dimensions to provide improved and/or imaging task-specific image information in a second image produced based upon the identified region-of-interest.

It may be appreciated that the second image of the object may represent different aspects of the object than the first image. By way of example, the second image of the object may represent merely a portion of what is represented in the first image, such as merely the region-of-interest portion. Moreover, the second image may be a zoomed-in view of the first image causing the second image to represent less of the object that the first image. Further, it may be appreciated that like the first image, the second image may be a two-, three-, four-, and/or five-dimensional representation of the object depending upon, among other things, the imaging modality utilized to examine the object and/or the projection data that is rebinned at 212 and utilized to generate the second image at 214.

It is also appreciated that while the above description has focused on generating a second image, obtained after review of a first image, the present disclosure is not intended to be limited to obtaining two images. Rather such a method 200 may be utilized for the generation of a sequence of images, the image processing and generation being dynamic and interactive in nature, given an acquired native projection data, for example.

The example method 200 ends at 216.

Figure 3:
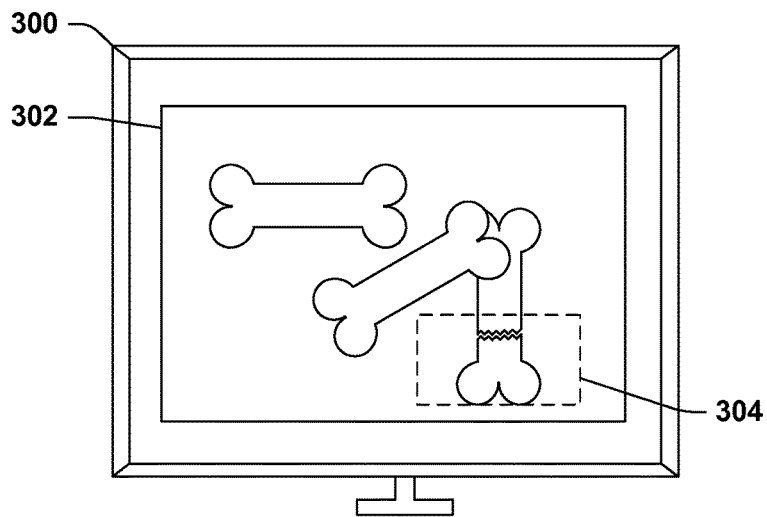
FIG. 3 illustrates an example user interface displaying a first image of an object and a region-of-interest window which may overlay at least some of a portion of the first image.

FIG. 3 illustrates a monitor 300 (e.g., 128 in FIG. 1) for presenting an example user interface comprising a first image 302 of an object presently or previously under examination by a radiology imaging modality. By way of example, in the context of security, a radiology imaging modality may be configured to examine baggage, and a first image 302, depicting at least a portion of a bag may be displayed on the monitor 300 for further inspection via security personnel, for example.

As provided herein, in one embodiment, a region-of-interest of the object may be identified from the first image 302. For example, in the illustrated embodiment, a region-of-interest window 304 (e.g., represented by dashed lines) may be presented/displayed to a user when a user selects an option to focus on a region-of-interest and/or may be presented by default. The region-of-interest window 304 typically defines that region-of-interest, such that the boundaries of the window 304 define boundaries of the region-of-interest, for example.

The region-of-interest window 304 may be configured to overlay at least some of an image, as shown in FIG. 3 with the window 304 overlaying a portion of the first image 302. Moreover, the window 304 may be moved about the image 302 and/or properties of the window 304 may be manipulated (e.g., the window 304 may be increased and/or decreased in size and/or shape to accommodate the varying sizes and/or shapes of objects of interest); the manipulation being either automatic or generated by interaction with the user, for example. By way of example and not limitation, a user may use a mouse to drag one or more boundaries of the window 304 to increase or decrease the size and/or shape of the window 304 and/or the user may select, in an options menu, for example, between predefined sizes for the window 304. Moreover, the user may use a mouse to reposition the window 304 relative to an underlying object. In this way, the window 304 can be maneuvered about the first image 302 and/or resized to identify a region-of-interest in the object as it is depicted in the first image 302, for example.

It may be appreciated that FIG. 3 and its accompanying description is merely intended to provide an example technique for identifying a region-of-interest. For example, in another embodiment, an automated process may be performed to identify one or more regions-of-interest of an object via a first image. For example, a threat detection system may be utilized to identify potential threat objects (e.g., regions-of-interest in a security application) from the first image based upon shape, density, atomic properties, and/or other properties. In such an example, it may be unnecessary to display a region-of-interest window 304 as provided for in FIG. 3, for example, because the region-of-interest is automatically identified. Although, it one embodiment, a region-of-interest window 304 may be displayed to a user to confirm the automatic identification of a region-of-interest (e.g., the region-of-interest window 304 may overlay the automatically identified region-of-interest, and a user may be given the option to confirm the automatic identification and/or to reject the automatic identification (e.g., and to manually adjust, reposition, resize, etc. the window 304)). It may be appreciated that the size and positioning of the region-of-interest may be dependent upon, among other things, the object of interest, as analyzed either automatically or by the user upon presentation of the first image data.

Figure 4:
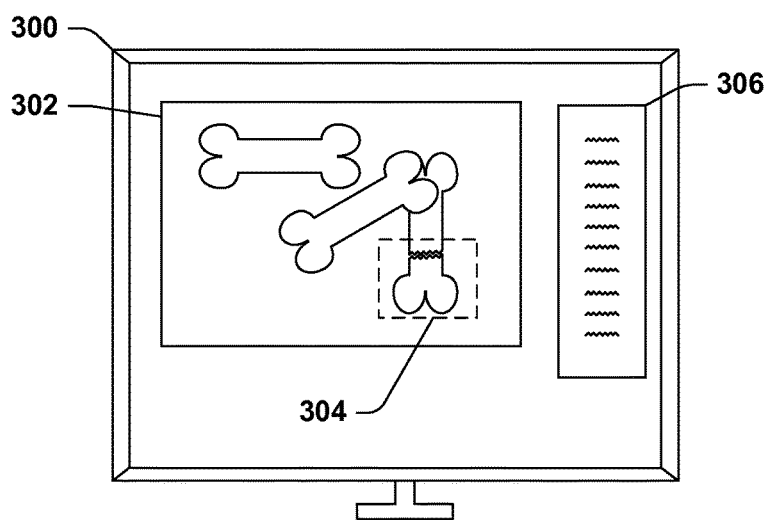
FIG. 4 illustrates an example user interface displaying a menu providing menu options for altering an appearance of a region-of-interest.

In one embodiment, a menu displaying options for altering an appearance of a region-of-interest (e.g., as represented in the first image obtained through either image reconstruction or image processing) may further be presented/displayed, and a user, for example, may select how to alter the appearance of the region-of-interest in a second image (e.g., generated from rebinning the native projection data). By way of example, FIG. 4 illustrates a user interface providing for a menu 306 that may be displayed upon the identification of a region-of interest (e.g., represented within the region-of-interest window 304) in a first image 302. However, in another embodiment, the menu 306 may be displayed before a region-of-interest is identified and/or maybe triggered based upon some other event besides the identification of a region-of-interest. For example, in one embodiment, a user may select an option from a toolbar which causes the menu 306 to be displayed. In another embodiment, an automatic region-of-interest analysis process may identify suggested options for second binning and processing, and highlight these options at the top of menu 306, for example.

As described with respect to FIG. 2, the menu 306 may provide a way for a user to specify how an appearance of a region-of-interest is to change (e.g., from the first image 302 to a second image). By way of example, the menu 306 may provide options for reducing artifacts in a second image, changing spatial resolution, changing contrast resolution, altering the energy spectrum of the image (e.g., from a single-spectral image to a multi-spectral image or set of images and/or vice-versa), and/or performing an automated analysis to determine desired properties of the second image (e.g., relative to the first image) based upon the identified region-of-interest. In this way, a user may select how an image is to be modified, or rather how the object is to be represented in a second image, for example. That is, stated differently, the selection of one or more menu options, along with the identification of a region-of-interest, for example, may be utilized to determine how the native projection data is to be rebinned and/or processed to create a second image representing the region-of-interest as desired (e.g., as specified via the selection of one or more options from the menu 306).

It may be appreciated that the presentation of a menu 306 and/or a user's selection of menu options describe merely one example technique for determining how data should be rebinned to present a representation of the region-of-interest that is different than an initial representation in the first image. For example, in another embodiment, the selection of one or more options for changing the appearance of a region-of-interest may be automated (e.g., such that the menu 306 is not presented on a display 300). By way of example, in one embodiment, the region-of-interest may be analyzed to determine properties of the region-of-interest (e.g., shape, density, z-effective, spatial frequency information content, streak artifact content, partial volume artifact content, spectral information content, etc. of aspects within the region-of-interest). Using such determined properties, computer-implemented software, for example, may determine desired properties for the second image or desired changes in the manner in which the region-of-interest is presented (e.g., relative to its presentation in the first image). Thus, in one embodiment, a user may have little to no direct, dynamic, and/or interactive input into how the region-of-interest is represented in the second image and/or may merely verify desired properties for the second image as determined by the computer-implemented software, for example.

Upon a region-of-interest being identified (e.g., as described with respect to FIG. 3) and/or desired properties of a second image being determined (e.g., as described with respect to FIG. 4), the native projection data may be accessed, rebinned, re-processed, and re-generated to generate a second image (e.g., as described with respect to FIG. 2) that at least partially represents the region-of-interest and that comprises the desired properties. It may be appreciated that in one embodiment, the creation of a second-image may occur dynamically (e.g., essentially in real-time) as the region-of-interest is identified and/or desired properties of the second image are determined. That is, stated differently, a second image may be displayed within mere fractions of a second of the region-of-interest being identified and/or of desired properties of the second image being determined. Of course, the generation/presentation of the second image may be dependent upon the amount of time necessary to rebin the native projection data and/or to generate the second image, which may depend upon processing capabilities and/or the amount of data being rebinned.

Further, it may be appreciated that while continued reference is made to identifying a region-of-interest in a first image (e.g., an initial image), it may be appreciated that the techniques and/or systems described herein may also be utilized to generate images subsequent to the first image. For example, in one embodiment, a region-of-interest may be identified in a first image and a second image may be subsequently generated at least partially representative of the region-of-interest. A user may then specify that one or more properties of the second image be changed (e.g., causing the native projection data to be rebinned for a second time and a third image to be generated) and/or may select a new region-of-interest from within the second image to cause a third image to be generated. In this way, a user may dynamically enlarge a region-of-interest (e.g., and magnify a particular aspect of the object) while also increasing the spatial resolution of respective, subsequent images, for example. That is, data may continually be manipulated in any desired manner(s) over any desired time frame(s), for example. A first image having first properties may be created at a first time, a second image having second properties may be created at a second time based upon at least some of the first image, a third image having third properties may be created at a third time based upon at least some of the first and/or second images, a fourth image having fourth properties may be created at a fourth time based upon at least some of the first, second and/or third images, etc.

Figure 5:
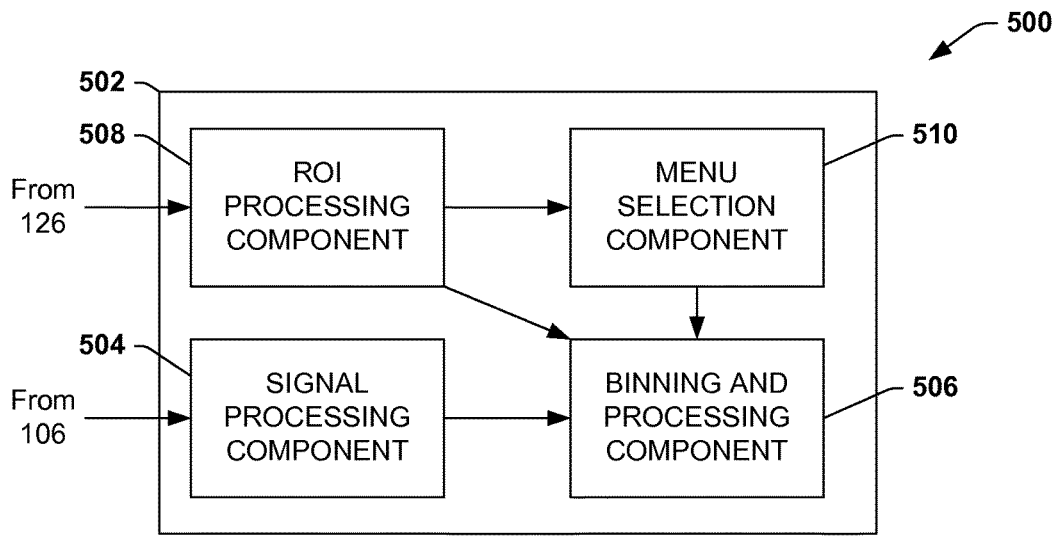
FIG. 5 illustrates an example photon data processor configured to rebin native projection data as a function of an identified region-of-interest.

FIG. 5 illustrates an example system 500 for use in a photon counting radiology imaging modality to generate a second image of an object based upon a region-of-interest identified from a first image of the object. More particularly, FIG. 5 illustrates example components of a photon data processor 502 (e.g., 122 in FIG. 1) configured to convert electrical signals produced by photon counting cells of a photon counting detector array into projection data and/or configured to bin/rebin the projection data to cause, upon re-generation, images comprising desired properties (e.g., a desired spatial resolution, desired contrast resolution, etc.) to be output. It may be appreciated that the illustrated system 500 is merely intended to describe example components and/or features thereof, and the disclosure is not intended to be limited to such an embodiment.

As illustrated, the example system 500 comprises a signal processing component 504 configured to utilize analog-to-digital converters to convert the electrical signals output by the cells of the detector array (e.g., 106 in FIG. 1) into projection data, which may be indicative of, among other things, a time respective photons were detected, an energy of respective photons, and/or a location of the cell that detected respective photons, for example.

The example system 500 further comprises a binning and processing component 506 configured to initially bin and/or rebin the projection data (e.g., referred to at times as native projection data) yielded from the signal processing component 504. That is, the binning and processing component 506 may organize and/or group the native projection data according to properties of the data (e.g., representative of detection events). For example, the native projection data may be grouped into bins according to, among other things, temporal, spatial, and/or energy properties of detection events represented by the data. It may be appreciated that, as previously described, the manner in which the native projection data is binned and/or processed may be a function of desired properties of an image generated from the binned data. By way of example, default properties of an initial image (e.g., such as a default spatial resolution, default image plane, etc.) may be specified and the native projection data may be initially binned accordingly to achieve the default properties of the initial image. Such defaults may be selected to provide a first image similar to what current charge-integrating modalities achieve, for example. Moreover, upon identification of the region-of-interest (as described above and as further described below), the binning and processing component 506 may be configured to rebin at least a portion of the native projection data to achieve desired properties (e.g., as specified by a user and/or determined automatically) of a second image, at least partially representing the identified region-of-interest.

The example system 500 further comprises a region-of-interest (ROI) processing component 508 configured to receive an indication of the region-of-interest. By way of example, when a region-of-interest is identified by a user (e.g., as described with respect to FIG. 3), an indication of the region-of-interest may be transmitted from a workstation (e.g., 126 in FIG. 1) to the ROI processing component 508. Further, the ROI processing component 508 may be configured to transmit information regarding the identified region-of-interest to the binning and processing component 506, where the binning and processing component 506 may use such information to determine how to rebin projection data and/or what native projection data to use during the rebinning, for example. The rebinned projection data may comprise data merely representative of the region-of-interest and/or may comprise native projection data that is not directly representative of the ROI (e.g., due to image generation requirements, such as filtered-backprojection reconstruction, which may require that native projection data not representative of the region-of-interest be rebinned). Moreover, it may be beneficial/necessary to combine native projection data not representative of the region-of-interest at a third level of binning, that is, at a level of binning different from that used to provide the first image and different from that used for second image, for example.

In yet another embodiment, the ROI processing component 508 may be configured to receive the first image (e.g., from the image generator 124 and/or from the workstation 126 (e.g., where the first image and/or data thereof was previously acquired and/or stored) in FIG. 1) and may be configured to identify a region-of-interest in the object as represented in the first image. By way of example, the ROI processing component 508 may utilize analytical, iterative, and/or other object identification techniques (e.g., such as threat-detection techniques) to analyze the first image to identify potential areas of interest based upon the application (e.g., security, cancer detection, heart imaging, etc.) of the imaging modality. Areas that the ROI processing component 508 identifies as potential areas of interest may be labeled as regions-of-interest and information regarding such regions-of-interest may be transmitted to the binning and processing component 506 from the ROI processing component 508, for example, for use during the rebinning of native projection data.

The example system 500 may further comprise a menu selection component 510 configured to receive a selection of a menu option(s) regarding desired changes to a representation of a region-of-interest relative to a first image produced from a first binning of the native projection data. That is, as described with respect to FIG. 4, in one embodiment, a menu may be presented to a user providing options describing modifications that may be made to the representation of the region-of-interest (e.g., to cause a new, second image of the region-of-interest to be generated). If the user makes a selection of one or more menu options from the presented menu, an indication of such may be transmitted from a workstation (e.g., 126 in FIG. 1) to a menu selection component 510, for example, configured to receive an indication of such a selection. Moreover, the menu selection component 510 may be configured to provide the binning and processing component 506 with information regarding the received indication, which may further assist the binning and processing component 506 in determining how to rebin/process data to cause an image, derived from the rebinned data, to correspond with the selected menu option(s), for example.

In one embodiment, menu selection component 510 may also be configured to receive user entered preference(s) for the rebinning and/or processing. Such preferences may also be imaging protocol dependent, for example.

It may be appreciated that the foregoing example system 500 is merely intended to describe components for one embodiment of a photon data processor 502, and is not intended to limit the scope of the disclosure, including the scope of the claims. For example, as described with respect to FIG. 2, a substantial amount of time (e.g., weeks) may elapse between an examination of an object and review of an image (e.g., particularly with respect to medical applications). Thus, image generation may take place with or without the patient being present (e.g., on an examination table). Therefore, the projection data generated by the signal processing component 504 may be stored in a storage medium prior to being binned and/or rebinned by the binning and processing component 506. Further, in some embodiments, automatic analysis may be performed to determine how to modify a representation of a region-of-interest in a first image to create a second image. Thus, in one such embodiment, the photon data processor may further comprise an image properties component configured to analyze the first image, or an identified region-of-interest therein, to determine how to modify the representation in view of the contents comprised in the region-of-interest. For example, where the image properties component identifies the region-of-interest as comprising both soft tissue and bone, the image properties component may determine that a higher spatial resolution is desired in a second image depicting the region-of-interest (e.g., relative to the first image). As such, the image properties component may provide information to the binning and processing component 506 for use in determining how to rebin data to achieve the desired high spatial resolution imagery, for example.

Figure 6:
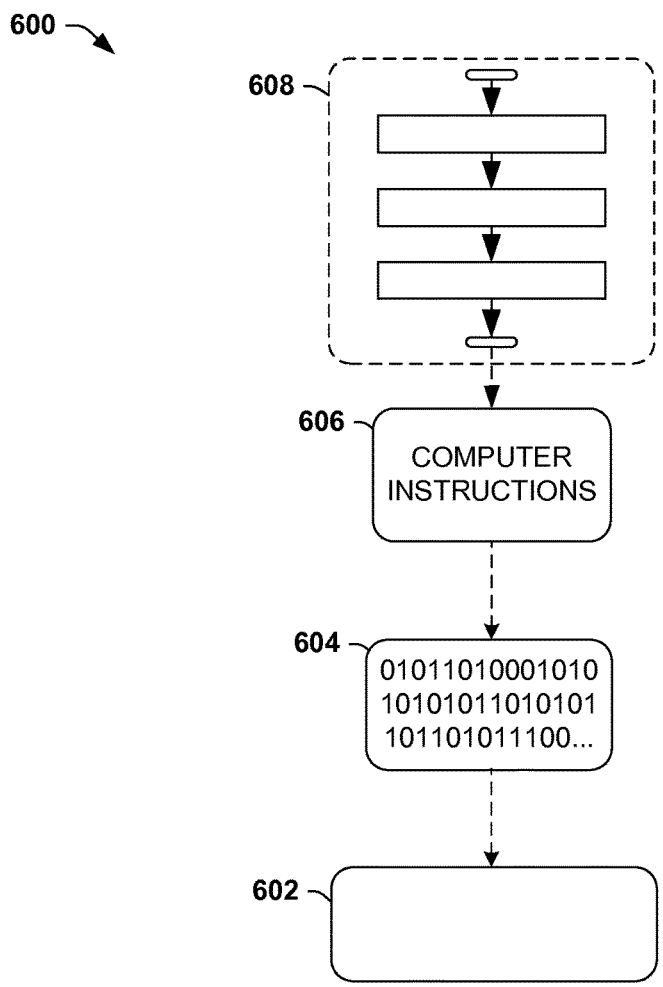
FIG. 6 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 6, wherein the implementation 600 comprises a computer-readable medium 602 (e.g., a CD-R, DVD-R, or a platter of a hard disk drive), on which is encoded computer-readable data 604. This computer-readable data 604 in turn comprises a set of computer instructions 606 configured to operate according to one or more of the principles set forth herein. In one such embodiment 600, the processor-executable instructions 606 may be configured to perform a method 608, such as at least some of the example method 200 of FIG. 2, for example. In another such embodiment, the processor-executable instructions 606 may be configured to implement a system, such as at least some of the exemplary scanner 100 of FIG. 1 and/or exemplary system 500 of FIG. 5, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method for reconstructing an image of a region-of-interest in an object under examination by a photon counting radiology imaging modality, comprising:
    binning projection data yielded from a photon counting detector into a first set of bins to create first binned data;
    reconstructing a first image of the object using the first binned data;
    identifying a region-of-interest in the object from the first image;
    rebinning at least a portion of the projection data into a second set of bins based upon the region-of-interest to create second binned data, wherein:
        each bin of the first set comprises projection data acquired from photon counting cells occupying a first amount of surface area of the photon counting detector,
        each bin of the second set comprises projection data acquired from photon counting cells occupying a second amount of surface area of the photon counting detector, and
    the second amount of surface area is smaller than the first amount of surface area; and
    reconstructing a second image of the object using the second binned data, the first image different than the second image;
    wherein the at least said portion of the projection data comprises a first portion of the projection data;
    the rebinning comprises:
        rebinning the first portion of the projection data into the second set of bins according to a first set of criteria to create the second binned data; and
        rebinning a second portion of the projection data into a third set of bins according to a second set of criteria different than the first set of criteria to create third binned data; and
    the reconstructing the second image comprising: reconstructing the second image of the object using the second binned data and the third binned data;
    wherein each bin of the third set comprises projection data acquired from photon counting cells occupying the first amount of surface area of the photon counting detector.

2. The method of claim 1, comprising displaying a region-of-interest window configured to overlay at least some of the first image and to be moved about the first image, the region-of-interest window defining the region-of-interest.

3. The method of claim 1, the second image only representative of the region-of-interest.

4. The method of claim 1, the second image comprising at least one of:
    a reduced number of artifacts in a portion of the second image representative of the region-of-interest relative to a number of artifacts of a portion of the first image representative of the region-of-interest;
    an increased contrast resolution of a portion of the second image representative of the region-of-interest relative to a contrast resolution of a portion of the first image representative of the region-of-interest; or
    an increased energy resolution of a portion of the second image representative of the region-of-interest relative to an energy resolution of a portion of the first image representative of the region-of-interest.

5. The method of claim 1, the second image providing a multispectral representation of the region-of-interest and the first image providing a single-spectral representation of the region-of-interest.

6. The method of claim 1, comprising:
    presenting a menu displaying menu options for altering an appearance of the region-of-interest as represented in the first image;
    receiving an indication of a selection from the menu options; and
    rebinning the projection data into the second set of bins according to the received indication.

7. The method of claim 1, comprising determining how to rebin the projection data to create the second binned data based upon features of the region-of-interest as represented in the first image.

8. The method of claim 7, the determining how to rebin the projection data to create the second binned data comprising:
    analyzing the region-of-interest as represented in the first image to identify features of the region-of-interest; and
    automatically determining how to rebin the projection data to create the second binned data based upon the identified features.

9. The method of claim 1, the at least a portion of the projection data rebinned to create the second binned data comprising merely projection data corresponding to the region-of-interest.

10. The method of claim 1, wherein:
the first image comprises at least one of a two-dimensional image, a three-dimensional image, a four dimensional image, or a five dimensional image, and
the second image comprises at least one of a two-dimensional image, a three-dimensional image, a four dimensional image, or a five dimensional image.

11. The method of claim 1, identifying a region-of-interest in the object from the first image comprising:
examining the first image to identify a representation of a desired aspect of the object, and the region-of-interest identified as a portion of the first image comprising the desired aspect of the object.

12. The method of claim 1, comprising:
emitting radiation towards the object while the object is under examination;
detecting at least a portion of the radiation that has traversed the object via the photon counting detector; and
generating the projection data based upon the detected radiation.

13. A non-transitory computer readable storage medium comprising computer executable instructions that when executed via a processor perform a method for reconstructing an image of a region-of-interest in an object under examination by a photon counting radiology imaging modality, the method comprising
binning projection data yielded from a photon counting detector into a first set of bins to create first binned data;
reconstructing a first image of the object using the first binned data;
identifying a region-of-interest in the object from the first image;
rebinning at least a portion of the projection data into a second set of bins based at least in part upon the region-of-interest to create second binned data;
wherein the at least said portion of the projection data comprises a first portion of the projection data;
the rebinning comprises:
rebinning the first portion of the projection data into the second set of bins according to a first set of criteria to create the second binned data; and
rebinning a second portion of the projection data into a third set of bins according to a second set of criteria different than the first set of criteria to create third binned data;
reconstructing a second image of the object using the second binned data and the third binned data, wherein:
the region-of-interest has a first spatial resolution in the first image and a second spatial resolution in the second image,
the second spatial resolution is greater than the first spatial resolution,
each bin of the first set comprises projection data acquired from photon counting cells occupying a first amount of surface area of the photon counting detector,
each bin of the second set comprises projection data acquired from photon counting cells occupying a second amount of surface area of the photon counting detector array,
the second amount of surface area is smaller than the first amount of surface area, and
each bin of the third set comprises projection data acquired from photon counting cells occupying the first amount of surface area of the photon counting detector.

14. A method for reconstructing an image of a region-of-interest in an object under examination by a photon counting radiology imaging modality, comprising:
binning projection data yielded from a photon counting detector into a first set of bins according to a first set of criteria to create first binned data;
reconstructing a first image of an object using the first binned data;
identifying a region-of-interest in the object from the first image;
rebinning a first portion of the projection data into a second set of bins according to a second set of criteria based upon the region-of-interest to create second binned data and rebinning a second portion of the projection data into a third set of bins according to a third set of criteria to create third binned data, wherein the second set of criteria is different than the third set of criteria; and
reconstructing a second image of the object using the second binned data and the third binned data;
wherein:
each bin of the first set comprises projection data acquired from photon counting cells occupying a first amount of surface area of the photon counting detector,
each bin of the second set comprises projection data acquired from photon counting cells occupying a second amount of surface area of the photon counting detector,
the second amount of surface area is smaller than the first amount of surface area, and
the first set of criteria and the third set of criteria are the same.

15. The method of claim 14, wherein a spatial resolution of the region-of-interest is greater in the second image than in the first image.

16. The method of claim 14, comprising displaying a region-of-interest window configured to overlay at least some of the first image and to be moved about the first image, the region-of-interest window defining the region-of-interest.

* * * * *